United States Patent
Feng et al.

(10) Patent No.: US 11,350,858 B2
(45) Date of Patent: Jun. 7, 2022

(54) ULTRA-SENSITIVE GLUCOSE SENSOR BASED ON GRAPHENE AND CARBON FIBER SUBSTRATE AND PREPARATION METHOD THEREOF

(71) Applicant: HARBIN INSTITUTE OF TECHNOLOGY, SHENZHEN, Shenzhen (CN)

(72) Inventors: Huanhuan Feng, Shenzhen (CN); Qing Liu, Shenzhen (CN); Xing Ma, Shenzhen (CN); Tingting Zheng, Shenzhen (CN); Weiwei Zhao, Shenzhen (CN); Jiaheng Zhang, Shenzhen (CN)

(73) Assignee: HARBIN INSTITUTE OF TECHNOLOGY, SHENZHEN, Shenzhen (CN)

( * ) Notice: Subject to any disclaimer, the term of this patent is extended or adjusted under 35 U.S.C. 154(b) by 419 days.

(21) Appl. No.: 16/707,196

(22) Filed: Jan. 8, 2020

(65) Prior Publication Data
US 2020/0178859 A1 Jun. 11, 2020

(51) Int. Cl.
| A61B 5/145 | (2006.01) |
| D01F 11/12 | (2006.01) |
| G01N 27/327 | (2006.01) |

(52) U.S. Cl.
CPC ........ *A61B 5/14532* (2013.01); *D01F 11/125* (2013.01); *G01N 27/3271* (2013.01); *G01N 27/3278* (2013.01); *A61B 2562/0285* (2013.01)

(58) Field of Classification Search
None
See application file for complete search history.

(56) References Cited

U.S. PATENT DOCUMENTS

2010/0028681 A1* 2/2010 Dai .................... B82Y 40/00
252/301.16

FOREIGN PATENT DOCUMENTS

CN 106970128 A 7/2017

OTHER PUBLICATIONS

Kazuki Hoshi et al., "Graphene-coated carbon fiber cloth for flexible electrodes of glucose fuel cells," 2016 Jpn. J. Appl. Phys. 5502BE05 (Year: 2016).*

* cited by examiner

*Primary Examiner* — Eric J Messersmith
(74) *Attorney, Agent, or Firm* — Bacon & Thomas, PLLC

(57) ABSTRACT

The present invention belongs to the technical field of material fabrication, and particularly relates to an ultra-sensitive glucose sensor based on a graphene and carbon fiber substrate and a fabrication method thereof. The method includes fabricating a carbon fiber cloth with vertical graphene growth on a surface thereof, performing pretreatment to make the carbon fiber cloth hydrophilic, directly soaking the carbon fiber cloth in a PBS solution of glucose oxidase with the pH of 7.4, and then taking out and drying the carbon fiber cloth at room temperature to obtain a glucose sensor. According to the present invention, the lower limit of glucose detection reaches about 0.1 mM, and the glucose sensor also has multistage corresponding characteristics, so that different detection coefficients and capabilities can be achieved in different glucose concentration ranges. The application range and precision of the glucose sensor are greatly improved.

10 Claims, 2 Drawing Sheets

ULTRA-SENSITIVE GLUCOSE SENSOR BASED ON GRAPHENE AND CARBON FIBER SUBSTRATE AND PREPARATION METHOD THEREOF

TECHNICAL FIELD

The present invention belongs to the technical field of material fabrication, and particularly relates to an ultra-sensitive glucose sensor based on a graphene and carbon fiber substrate and a fabrication method thereof.

BACKGROUND

At present, a carbon fiber cloth is widely used as a flexible sensor substrate material due to its flexibility and chemical stability. There are numerous electrochemical sensors based on carbon fiber cloth in the market. Due to a huge market demand and mild detection conditions, glucose electrochemical sensors have been commercially produced on a large scale. However, the glucose electrochemical sensors in the market have different quality and low sensitivity, which greatly limits their application in high-end biochemical detection.

Especially, the rise of several emerging industries such as flexible electronics, wearable and big health imposes a higher demand on ultra-low concentration and ultra-high sensitivity sensors. However, existing products cannot meet the performance requirements of the market. Therefore, based on ultra-sensitive detection, according to the present invention, glucose electrochemical detectors with ultra-sensitive detection capability are successfully prepared by fabricating a carbon fiber cloth with vertically-functionalized graphene on a surface thereof.

For example, CN106970128A discloses a glucose detector with flexible ZnO nanocrystal composite carbon fiber and graphene oxide and a fabrication method thereof. The sensor sequentially includes a carbon fiber, graphene oxide and a ZnO nanocrystal layer from bottom to top. The fabrication method includes: firstly fabricating carbon fiber composite graphene oxide as a substrate, and then growing ZnO nanocrystals on the substrate at a certain temperature to self-assemble into the glucose detector with the flexible ZnO nanocrystal composite carbon fiber and graphene oxide. The lower detection limit is about 5 mM, and the detection sensitivity needs to be further improved.

SUMMARY

In view of the problems existing in the prior art, the present invention provides an ultra-sensitive glucose electrochemical sensor based on a graphene and carbon fiber substrate, which has an ultra-low detection concentration and ultra-high sensitivity. The sensor can meet the stringent requirements for electronic body surface data acquisition of emerging wearable products and have the detection capability.

According to the present invention, the lower limit of glucose detection reaches about 0.1 mM, and the sensor also has multistage corresponding characteristics, so that different detection coefficients and capabilities can be achieved in different glucose concentration ranges. The application range and precision of the sensor can be greatly improved.

Specifically, the present invention is implemented through the following technical solution:

A method for fabricating an ultra-sensitive glucose sensor based on a graphene and carbon fiber substrate, including the following steps:

(1). Selecting and pretreating a graphene and carbon fiber cloth (GR/CC):

selecting a graphene and carbon fiber cloth, and sequentially soaking the graphene and carbon fiber cloth in isopropanol, $H_2SO_4$ solution and deionized water to make the graphene and carbon fiber cloth hydrophilic; and (2). Soaking in a solution:

soaking the pretreated graphene and carbon fiber cloth in a glucose oxidase (GOD) solution, and taking out and drying the graphene and carbon fiber cloth to obtain a glucose sensor (GOD/GR/CC).

Preferably, the graphene and carbon fiber cloth is a carbon fiber cloth (GR/CC) with vertical graphene grown and is prepared by using a thermal CVD method. Specifically, vapor deposition of graphene is carried out for 10 h at 1100° C. in an atmosphere with 95% $CH_4$ and 5% $H_2$.

Through a large number of experimental studies, it is found that the adopted carbon fiber cloth with graphene vertically grown on the surface according to the foregoing solution has strong adhesion, and the electrochemical detection capability is excellent after adhesion of glucose oxidase.

Preferably, step (1) is preferably to select and soak the graphene and carbon fiber cloth sequentially in isopropanol, 0.1 M $H_2SO_4$ solution and deionized water for 30 min respectively to make the graphene and carbon fiber cloth hydrophilic. The method has good effect and simple post-treatment. The hydrophilicity can be formally determined by testing a surface contact angle. In a process groping stage, the wetting and spreading ability of water to the carbon fiber cloth before and after treatment can be simply compared, and a process operation window can be selected.

Preferably, step (2) is preferably to soak the pretreated graphene and carbon fiber cloth in the GOD solution at 4° C. for 72 h, shake the solution intermittently, and finally take out and dry the graphene and carbon fiber cloth at room temperature to obtain a glucose sensor (GOD/GR/CC).

Through a large number of experimental studies, it is found that soaking at a temperature of 4° C. can ensure that an enzyme does not lose its activity. The soaking time is 72 h to ensure completed and firm adsorption.

Preferably, a shaking frequency of a shaking table is 0.5 Hz. This shaking condition is used for intermittent shaking to increase the diffusion capacity of the system and avoid uneven concentration in local areas.

Another objective of the present invention is to provide an ultra-sensitive glucose sensor based on a graphene and carbon fiber substrate. The ultra-sensitive glucose sensor is prepared by using the foregoing fabrication method.

Relative to the prior art, the beneficial effects of the present invention are as follows.

(1) According to the present invention, the carbon fiber cloth with the vertical graphene grown on the surface is used, and the glucose sensor is prepared through simple physical adsorption. The fabrication method is simple, and has a great application prospect in detecting a lower glucose concentration.

(2) In the preliminary research of the present invention, it was found that if no vertical graphene was grown on the surface of the carbon fiber cloth through the foregoing fabrication method, it was difficult to adsorb glucose oxidase, and the carbon fiber cloth could not be applied to glucose detection.

(3) The glucose sensor of the present invention is use for detecting glucose. It is found that the glucose sensor shows excellent detection performance under ultra-low concentration glucose, has high detection sensitivity and multistage corresponding performances, and is expect to be widely applied in the field of flexible electronics-based biomedical detection.

BRIEF DESCRIPTION OF THE DRAWINGS

FIG. 4b) is a scatter diagram of a corresponding peak current and a glucose concentration, where DPV parameters are: increased potential of 5 mV, amplitude of 25 mV, pulse width of 0.2 s, and pulse period of 0.5 s; FIG. 5b) is a scatter diagram of a corresponding peak current and a glucose concentration, where a CV parameter is: a scanning speed of 200 mV.

DETAILED DESCRIPTION

The present invention will be described in further detail below with reference to embodiments and accompanying drawings, but embodiments of the present invention are not limited thereto.

Figure 1:
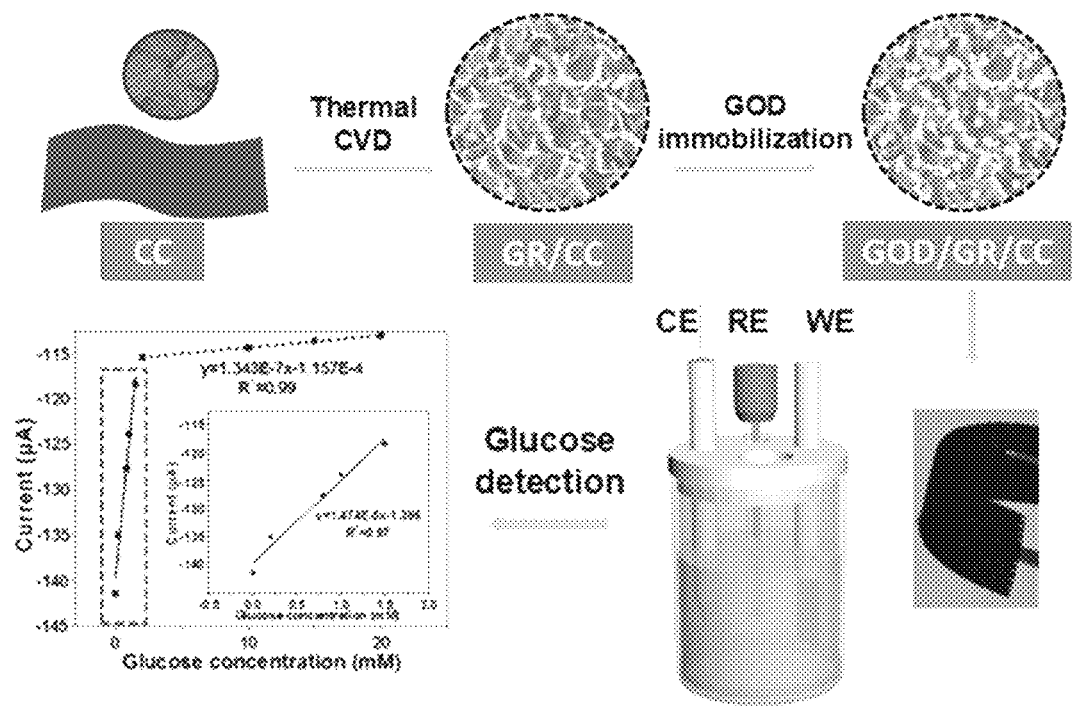
FIG. 1 is a schematic flow chart of fabrication material composition of a glucose sensor according to the present invention.
Figure 3:
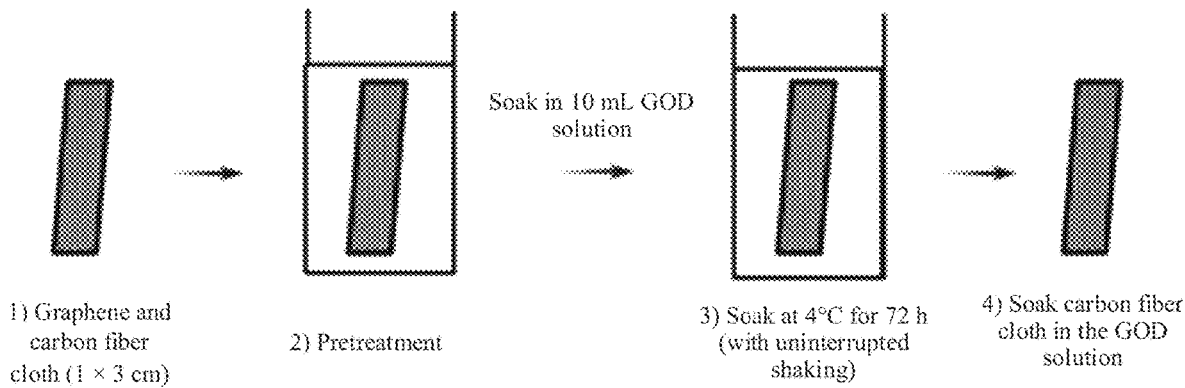
FIG. 3 is a schematic flow chart of a glucose sensor fabrication process according to the present invention.

Embodiment 1 Ultra-Sensitive Glucose Sensor Based on a Graphene and Carbon Fiber Substrate and a Fabrication Method Thereof A reference is made to schematic fabrication diagrams of the glucose sensor of the present invention shown in FIGS. 1 and 3.

(1) A graphene and carbon fiber cloth was selected and pretreated:

A 1×3 cm graphene and carbon fiber cloth was selected and sequentially soaked in isopropanol, 0.1 M $H_2SO_4$ solution and deionized water for 30 min respectively to make the graphene and carbon fiber cloth hydrophilic.

Figure 2:
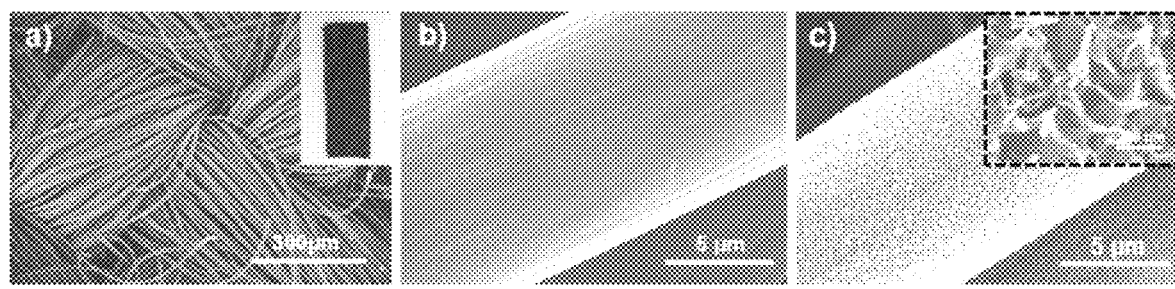
FIG. 2 shows SEM images of a graphene and carbon fiber cloth prepared according to the present invention, FIG. 2a) shows an SEM image of the carbon fiber cloth under low resolution, FIG. 2b) shows an SEM image of the carbon fiber cloth under high resolution, and FIG. 2c) is an SEM image of the carbon fiber cloth with graphene vertically grown on a surface thereof under high resolution.

The graphene and carbon fiber cloth was a carbon fiber cloth (GR/CC) with vertical graphene grown and was prepared by using a thermal CVD method. Specifically, vapor deposition of graphene was carried out for 10 h at 1100° C. in an atmosphere with 95% $CH_4$ and 5% $H_2$. SEM images of the graphene and carbon fiber cloth are as shown in FIG. 2, where FIG. 2a) shows an SEM image of the carbon fiber cloth under low resolution, FIG. 2b) shows an SEM image of the carbon fiber cloth under high resolution, and FIG. 2c) is an SEM image of the carbon fiber cloth with graphene vertically grown on a surface thereof under high resolution.

(2) The graphene and carbon fiber cloth was soaked in a solution:

The pretreated graphene and carbon fiber cloth was soaked in the GOD solution (the solution was 0.1 M PBS solution with the pH of 7.4) at 4° C. for 72 h. The solution was shaken intermittently. A shaking frequency of a shaking table was 0.5 Hz. Finally the graphene and carbon fiber cloth was taken out and dried at room temperature to obtain a glucose sensor (GOD/GR/CC).

Embodiment 2 Performance Testing

The glucose sensor prepared in Embodiment 1 was placed in a three-electrode system with electrolyte being the 0.1 M PBS solution with the pH of 7.4, a working electrode being GOD/GR/CC, a counter electrode being a Pt plate, and a reference electrode being a saturated calomel electrode to measure the glucose concentration.

Figure 4:
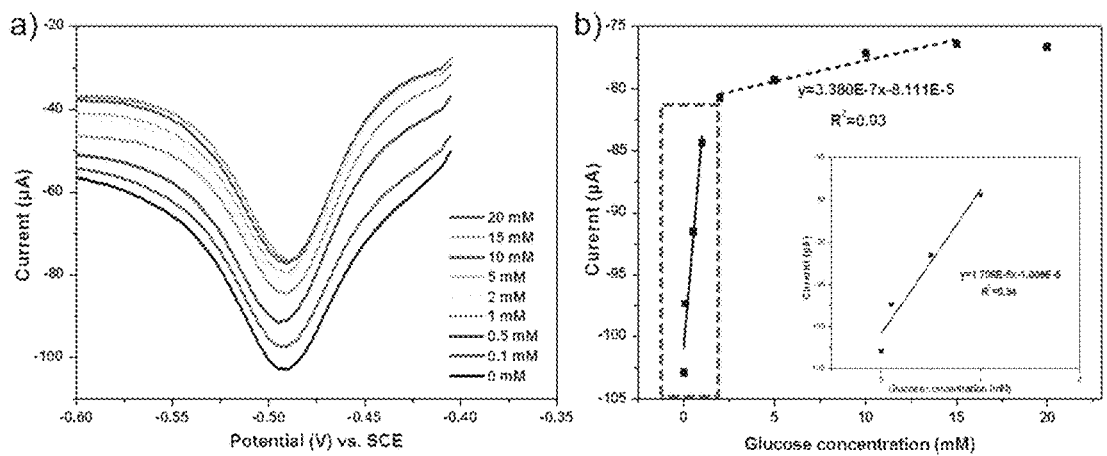
FIG. 4 is a graph of experimental data measured by differential pulse voltammetry (DPV), where FIG. 4a) shows DPV curves of the GOD/GR/CC in 0.1 M PBS solution with the pH of 7.4, and the curves show measurement results under 0 mM to 20 mM respectively from bottom to top.

FIG. 4 is a graph of experimental data measured by differential pulse voltammetry (DPV). It can be seen that the sensitivity of the glucose sensor is high under low concentration. The GOD/GR/CC is 1.7 $\mu A\ mM^{-1}\ cm^{-2}$ (0-1 mM). The lower detection limit of the sensor can reach 0.1 mM, thus greatly improving the lower detection limit of glucose.

Figure 5:
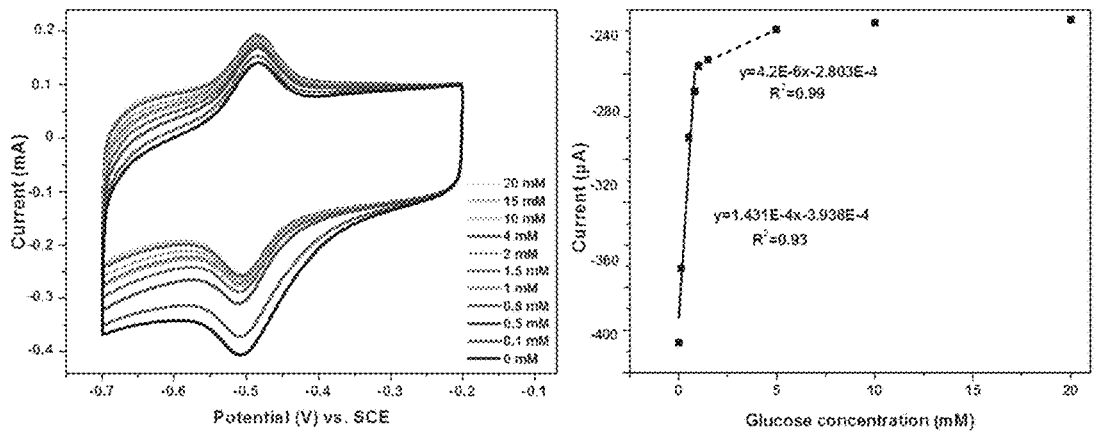
FIG. 5 is a graph of experimental data measured by cyclic voltammetry (CV), where FIG. 5a) shows CV curves of the GOD/GR/CC in 0.1 M PBS solution with the pH of 7.4, and the curves show measurement results under 0 mM to 20 mM respectively from bottom to top.

FIG. 5 is a graph of experimental data measured by cyclic voltammetry (CV). It can be seen that the sensitivity of the glucose sensor is high under low concentration. The GOD/GR/CC is 14.3 $\mu A\ mM^{-1}\ cm^{-2}$ (0-1 mM). The lower detection limit of the sensor can reach 0.1 mM, thus greatly improving the lower detection limit of glucose.

The foregoing results fully demonstrate that the sensor of the present invention also realizes multistage performance correspondence. The sensor has an ultra-large linear correlation coefficient in an ultra-low concentration stage to realize accurate concentration detection, and has a suitable linear correlation coefficient in a medium glucose concentration range to realize a larger detection range.

The foregoing embodiments are preferred embodiments of the present invention. However, the embodiments of the present invention are not limited by the foregoing embodiments. Any other change, modification, replacement, combination and simplification made without departing from the spiritual essence and principle of the present invention should be equivalent substitution manners, and shall all fall within the protection scope of the present invention.

What is claimed is:

1. A method for fabricating an ultra-sensitive glucose sensor based on a graphene and carbon fiber substrate, comprising the following steps:

(1). Selecting and pretreating a graphene and carbon fiber cloth by
selecting a graphene and carbon fiber cloth, and sequentially soaking the graphene and carbon fiber cloth in isopropanol, $H_2SO_4$ solution and deionized water to make the graphene and carbon fiber cloth hydrophilic; and (2). Soaking in a solution by
soaking the pretreated graphene and carbon fiber cloth in a glucose oxidase (GOD) solution, and taking out and drying the graphene and carbon fiber cloth to obtain a glucose sensor (GOD/GR/CC).

2. The fabrication method according to claim 1, wherein the graphene and carbon fiber cloth is a carbon fiber cloth (GR/CC) with vertical graphene grown and is prepared by using a thermal CVD method, and specifically, vapor deposition of graphene is carried out for 10 h at 1100° C. in an atmosphere with 95% $CH_4$ and 5% $H_2$.

3. The fabrication method according to claim 1, wherein step (1) comprises selecting and soaking the graphene and carbon fiber cloth sequentially in isopropanol, 0.1 M $H_2SO_4$ solution and deionized water for 30 min respectively to make the graphene and carbon fiber cloth hydrophilic.

4. The fabrication method according to claim 1, wherein step (2) comprises soaking the pretreated graphene and carbon fiber cloth in the GOD solution at 4° C. for 72 h, shaking the solution intermittently, and finally taking out and drying the graphene and carbon fiber cloth at room temperature to obtain a glucose sensor (GOD/GR/CC).

5. The fabrication method according to claim 1, shaking with a shaking frequency of a shaking table of 0.5 Hz.

6. An ultra-sensitive glucose sensor based on a graphene and carbon fiber substrate, wherein the ultra-sensitive glucose sensor is prepared by using the fabrication method according to claim 1.

7. An ultra-sensitive glucose sensor based on a graphene and carbon fiber substrate, wherein the ultra-sensitive glucose sensor is prepared by using the fabrication method according to claim 2.

8. An ultra-sensitive glucose sensor based on a graphene and carbon fiber substrate, wherein the ultra-sensitive glucose sensor is prepared by using the fabrication method according to claim 3.

9. An ultra-sensitive glucose sensor based on a graphene and carbon fiber substrate, wherein the ultra-sensitive glucose sensor is prepared by using the fabrication method according to claim 4.

10. An ultra-sensitive glucose sensor based on a graphene and carbon fiber substrate, wherein the ultra-sensitive glucose sensor is prepared by using the fabrication method according to claim 5.

* * * * *